United States Patent [19]

Groenwold

[11] E Patent Number: Re. 32,483

[45] Reissued Date of Patent: Aug. 25, 1987

[54] SYNERGISTIC HERBICIDAL COMBINATION

[75] Inventor: Bareld E. Groenwold, Los Altos, Calif.

[73] Assignee: Stauffer Chemical Co., Westport, Conn.

[21] Appl. No.: 832,115

[22] Filed: Feb. 24, 1986

Related U.S. Patent Documents

Reissue of:

[64] Patent No.: 4,456,472
Issued: Jun. 26, 1984
Appl. No.: 444,959
Filed: Nov. 29, 1982

[51] Int. Cl.[4] ..... A01N 37/18
[52] U.S. Cl. ..... 71/118
[58] Field of Search ..... 71/118

[56] References Cited

U.S. PATENT DOCUMENTS

| | | | |
|---|---|---|---|
| 3,690,865 | 9/1972 | Ahle | 71/118 |
| 3,707,366 | 12/1972 | Cahoy | 71/118 |
| 3,718,455 | 2/1973 | Baker et al. | 71/118 |
| 4,001,004 | 1/1977 | Toyama et al. | 71/118 |
| 4,008,069 | 8/1977 | Ahle | 71/118 |

FOREIGN PATENT DOCUMENTS

| | | |
|---|---|---|
| 2453912 | 5/1975 | Fed. Rep. of Germany . |
| 7928450 | 8/1971 | Japan . |
| 7928454 | 5/1971 | Japan . |
| 51-12925 | 1/1976 | Japan . |

OTHER PUBLICATIONS

Aggour, Chem. Abst., vol. 96 (1982), 15975c.
Pesticide Manual, 6th Edition (1979), pp. 61 and 378, British Crop Protection Council.

*Primary Examiner*—Catherine L. Mills
*Attorney, Agent, or Firm*—Michael J. Bradley; J. G. Ackerman

[57] ABSTRACT

A mixture of the herbicides napropamide and butam has been found to exhibit synergistic results, particularly in pre-emergence surface application or pre-plant incorporation, and for controlling weeds in the presence of a rapeseed crop.

5 Claims, No Drawings

SYNERGISTIC HERBICIDAL COMBINATION

Matter enclosed in heavy brackets [ ] appears in the original patent but forms no part of this reissue specification; matter printed in italics indicates the additions made by reissue.

This invention relates to a herbicidal combination of two known herbicides, napropamide and butam, each of which is known to be effective for certain purposes, but which combination has been found to possess unexpected synergistic properties.

Napropamide, 2-(α-napthoxy)-N,N-diethylpropionamide,

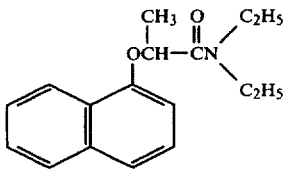

is a commercial herbicide sold under the registered trademark Devrinol ® and is described as a herbicide with both pre-emergence and post-emergence activity in U.S. Pat. Nos. 3,480,671, 3,718,455, and 3,998,880, for instance. These patents also contain methods of preparing this compound.

Butam, N-benzyl-N-isopropylpivalamide,

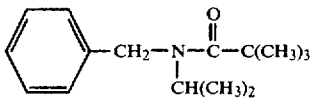

is described, for instance, in U.S. Pat. Nos. 3,707,366 and 3,974,218, which contain methods for its preparation. The compound is known to be an effective pre-emergence herbicide for controlling annual grassy weeds in certain crops, including soybeans, rapeseed, cotton and others.

It has now been found that a combination of napropamide and butam, containing these two substances in a weight ratio respectively of about 2:1 to about 1:2, possesses synergistic activity in controlling weeds, in general, and in the presence of a rapeseed crop. This synergistic activity is exhibited most particularly at application rates of from about 0.25 to about 1.5 pounds per acre (about 0.28 to about 1.68/ha) of either or both compounds.

The following examples demonstrate the synergistic herbicidal response of such compositions.

EXAMPLE 1

(Greenhouse Evaluation—Pre-emergence Surface Treatment)

This example demonstrates the synergistic response of combinations of napropamide and butam in combined pre-emergence surface application to a variety of weeds planted in the presence of a rapeseed crop.

Flats were filled to a depth of 3 inches (7.6 cm) with loamy sand soil containing 50 parts per million (ppm) each of a fungicide and 18-18-18 fertilizer. Seeds of rapeseed (Brassica napobrassica) and six weed species were planted in individual rows using one species per row across the width of the flat. The seeds were covered with soil. The weeds used were annual ryegrass (Lolium multiflorum), barnyardgrass (Echinochloa crusgalli), green foxtail (Setaria viridis), lambsquarter (Chenopodium album), pigweed (Amaranthus retroflexus), and wild buckwheat (Polygonum convolvulus). The seeds were planted to give about 20 to 50 seedlings per row after emergence, depending on the size of the plants.

Compositions were prepared for testing by weighing out 20 mg. respectively of napropamide and butam, and dissolving each portion in 3 ml. of acetone which contained 1% polyoxyethylene sorbitan monolaurate emulsifying agent. The solution was then sprayed uniformly on the soil in the flat one day after planting the seeds, at application rates ranging from 0.25 to 0.5 pounds per acre (0.28 to 0.56 kg/ha). After treatment the flats were placed in a greenhouse at a temperature of 70°-85° F. and watered by sprinkling. Two weeks after treatment the degree of injury or control was determined by comparison of untreated check plants of the same age. The injury rating, on a scale of 0 to 100%, was recorded for each species as percent control, with 0% representing no injury and 100% representing complete kill.

The results of these tests are contained in the following Table I. Under the heading "O" are given the ratings for the compounds applied as observed. Under the heading "E" are provided the expected results for combinations of the two herbicides, based on the response for each herbicide alone, derived from this data using Limpel's formula, namely, $$E = X + Y - \frac{XY}{100}$$

where

X = the observed percent injury when one of the herbicides is used alone and

Y = the observed percent injury when the other herbicide is used alone.

This formula is contained in the article "Weed Control by Dimethylchloroterephthalate Alone and in Certain Combinations," Limpel et al., Proc. NEWCC., Vol. 16, pp. 48–53 (1962). When the observed result exceeds the result which would have been expected using this formula, synergism is demonstrated.

TABLE I

| Napropamide | Butam | Rapeseed | | Annual ryegrass | | Barnyard grass | | Foxtail | | Lambsquarter | | Pigweed | | Wild Buckwheat | |
|---|---|---|---|---|---|---|---|---|---|---|---|---|---|---|---|
| | | O | E | O | E | O | E | O | E | O | E | O | E | O | E |
| 0.25 | — | 0 | | 0 | | 20 | | 0 | | 20 | | 0 | | 0 | |
| 0.50 | — | 0 | | 45 | | 65 | | 50 | | 70 | | 50 | | 30 | |
| — | 0.25 | 0 | | 20 | | 30 | | 20 | | 10 | | 5 | | 0 | |

TABLE I-continued

| Napropamide | Butam | Rapeseed O | Rapeseed E | Annual ryegrass O | Annual ryegrass E | Barnyard grass O | Barnyard grass E | Foxtail O | Foxtail E | Lambsquarter O | Lambsquarter E | Pigweed O | Pigweed E | Wild Buckwheat O | Wild Buckwheat E |
|---|---|---|---|---|---|---|---|---|---|---|---|---|---|---|---|
| — | 0.50 | 0 | | 30 | | 65 | | 20 | | 30 | | 40 | | 0 | |
| 0.25 | 0.25 | 0 | 0 | 50 | 20 | 80 | 44 | 30 | 20 | 65 | 28 | 50 | 5 | 10 | 0 |
| 0.25 | 0.50 | 0 | 0 | 78 | 30 | 90 | 72 | 60 | 20 | 68 | 44 | 40 | 40 | 30 | 0 |
| 0.50 | 0.25 | 0 | 0 | 85 | 56 | 85 | 75 | 78 | 60 | 75 | 73 | 55 | 52 | 50 | 30 |

EXAMPLE 2

(Field Tests, Pre-plant Incorporation)

Sprayable solutions containing napropamide and butam were prepared by mixing a wettable powder containing approximately 50 weight % napropamide with an emulsifiable concentrate containing approximately 6 pounds per gallon (0.72 kg per liter) butam, and water. The solution was sprayed on field test plots in various locations in France, West Germany, and Great Britain, at an application rate of 0.75 kg/ha (0.67 lb/acre) napropamide and 1.44 kg/ha (1.28 lb/acre) butam. After spraying, the soil was filled to incorporate the herbicidal mixture, and was then planted with rapeseeds. Other plots at the same locations were similarly treated with napropamide and butam alone, at the same rates before planting, and one plot was left untreated as a check. Tests were conducted during the fall season.

Undesirable vegetation which appeared in the plots included:

France: volunteer barley, volunteer wheat, Alopercurus myosuroides, Matricaria chamomilla, Sinapis arvensis, Veronica persica, Veronica hederaefolia Germany: volunteer barley, Alopecurus myosuroides, Galium aparine, Lamium amplexicaule, Matricaria chamomilla, Stellaria media, viola arvensis Great Britain: volunteer barley, Alopecurus myosuroides, Matricaria spp., Senecio vulgaris, Stellaria media Results of these tests are contained in the following Tables II–IV. Control of weeds and phytotoxic effect on crops were determined by visual comparison with the untreated check plots. In all cases, the combination of napropamide and butam resulted in little or no damage to the rapeseed crop.

Synergistic control effects were found in West Germany in volunteer barley and in France of Sinapis arvensis. In a number of the tests, the control of a given weed by one of the two compounds was sufficiently high so as to leave no effective possibility of improvement at the application rates. Limpel's Formula was used as above in determining synergistic activity.

TABLE II

| Compounds and Application Rates (kg/ha) | FRANCE Control, % Volunteer barley | Volunteer wheat | *Alopecurus myosuroides* | *Matricaria chamomilla* | *Sinapis arvensis* | *Veronica persica* | *Veronica hedeaefolia* |
|---|---|---|---|---|---|---|---|
| Napropamide, 0.75 | 100 | 56 | 95 | 87 | 50 | 90 | 96 |
| Butam, 1.44 | 79 | 79 | 97 | 87 | 0 | 85 | 39 |
| Napropamide, 0.75 + Butam, 1.44 | 96 | 79 | 98 | 87 | 76* | 86 | 98 |

*Expected Control - 50%

TABLE III

| Compounds and Application Rates (kg/ha) | WEST GERMANY Control, % Volunteer barley | *Alopecurus myosuroides* | *Galium aparine* | *Lamium amplexicaule* | *Matricaria chamomilla* | *Stellaria media* | *Viola arvensis* |
|---|---|---|---|---|---|---|---|
| Napropamide, 0.75 | 40 | 50 | 20 | 43 | 78 | 71 | 10 |
| Butam, 1.44 | 60 | 50 | 60 | 46 | 61 | 77 | 10 |
| Napropamide, 0.75 + Butam, 1.44 | 95* | 70 | 40 | 71 | 94 | 93 | 43** |

*Expected control - 76%
**Expected control - 20%

TABLE IV

| Compounds and Application Rate (kg/ha) | GREAT BRITAIN Control, % Volunteer barley | *Alopecurus myosuroides* | Matricaria spp. | *Senecio vulgaris* | *Stellaria media* |
|---|---|---|---|---|---|
| Napropamide, 0.75 | 25 | 74 | 59 | 87 | 54 |
| Butam, 1.44 | 54 | 79 | 14 | 0 | 60 |
| Napropamide, 0.75+ Butam, 1.44 | 66 | 90 | 66 | 86 | 66 |

Compositions containing the two herbicides napropamide and butam may be prepared in a number of conventional ways. Butam is a colorless oil, insoluble in water but very soluble in ethanol, benzene and toluene, and is commercially marketed in the form of an emusifiable concentrate. Napropamide is a solid and is commercially marketed in several forms including granular, wettable powder, and flowable (concentrated aqueous suspension). Formulations or compositions for applying the two herbicides in combination may be prepared, for instance, by mixing a wettable powder containing napropamide (50 weight percent) with an emulsifiable concentrate containing butam, in water, to prepare a sprayable solution. The amounts of water, napropamide and butam, are selected so as to provide solutions containing the desired ratio of napropamide to butam and for application at the desired rate.

Alternatively, a herbicide composition containing napropamide and butam can be prepared from the technical grade herbicides, with suitable adjuvants, and then mixed with water to form a sprayable solution. An example of such a composition is:

| Component | Weight % |
|---|---|
| napropamide, technical grade (93% pure) | 14.2 |
| butam, technical grade (95% pure) | 33.3 |
| 1,1,1-trichloroethane | 47.6 |
| surfactants | 4.9 |
| Total | 100.0 |

What is claimed is:

1. A synergistic herbicidal composition comprising a mixture of herbicidally effective amounts of napropamide and butam, in a weight ratio of between about 2:1 and about [1:2] *1:2.4.*

2. A composition according to claim 1 in which the weight ratio of napropamide to butam is about 2:1.

3. A composition according to claim 1 in which the weight ratio of napropamide to butam is about 1:1.

4. A composition according to claim 1 in which the weight ratio of napropamide to butam is about 1:2.

*5. A composition according to claim 1 in which the weight ratio of napropamide to butam is between about 2:1 to about 1:2.*

* * * * *